(12) United States Patent
Yamagata et al.

(10) Patent No.: US 7,842,239 B2
(45) Date of Patent: Nov. 30, 2010

(54) ANALYZER-FEEDING DEVICE

(75) Inventors: Hidenari Yamagata, Kyoto (JP);
Tomohiro Demura, Kyoto (JP);
Masahiro Hanafusa, Kyoto (JP)

(73) Assignee: Arkray, Inc., Kyoto (JP)

( * ) Notice: Subject to any disclaimer, the term of this patent is extended or adjusted under 35 U.S.C. 154(b) by 1316 days.

(21) Appl. No.: 10/544,089

(22) PCT Filed: Jan. 27, 2004

(86) PCT No.: PCT/JP2004/000724

§ 371 (c)(1),
(2), (4) Date: Jul. 28, 2005

(87) PCT Pub. No.: WO2004/068145

PCT Pub. Date: Aug. 12, 2004

(65) Prior Publication Data

US 2006/0057024 A1    Mar. 16, 2006

(30) Foreign Application Priority Data

Jan. 31, 2003    (JP)  .............................. 2003-023079

(51) Int. Cl.
*G01N 15/06* (2006.01)
*G01N 21/00* (2006.01)
*G01N 27/00* (2006.01)

(52) U.S. Cl. ...................... 422/68.1; 422/63; 422/82.01
(58) Field of Classification Search ................ 422/68.1, 422/63, 82.01
See application file for complete search history.

(56) References Cited

U.S. PATENT DOCUMENTS

| | | | |
|---|---|---|---|
| 4,279,514 A | 7/1981 | Blumel et al. | |
| 4,796,744 A | 1/1989 | Sanger | |
| 4,876,204 A | 10/1989 | Inoue et al. | |
| 5,470,533 A | 11/1995 | Shindo et al. | |
| 5,510,266 A * | 4/1996 | Bonner et al. | ................. 436/43 |
| 5,552,116 A | 9/1996 | Yokota et al. | |
| 5,556,597 A | 9/1996 | Shindo et al. | |
| 2002/0057993 A1 * | 5/2002 | Maisey et al. | ............ 422/82.01 |

FOREIGN PATENT DOCUMENTS

| | | |
|---|---|---|
| EP | 0049617 | 5/1983 |
| JP | 57-57663 | 12/1982 |
| JP | 58-216819 | 12/1983 |

(Continued)

*Primary Examiner*—Lore Jarrett
(74) *Attorney, Agent, or Firm*—Hamre, Schumann, Mueller & Larson, P.C.

(57) ABSTRACT

The present invention relates to a test tool feeder (X1) including a storage portion for storing a plurality of test tools (4A, 4B), and a transporting member (2) provided with at least one loading portion (21, 22) for loading the test tools (4A, 4B) stored in the storage portion, where the transporting member transports the test tools (4A, 4B) one by one. The storage portion includes a plurality of storage spaces (11, 12) each storing a plurality of test tools (4A, 4B). Preferably, in the test tool feeder (X1), with respect to each of the storage spaces (11, 12), selection can be made between a state in which the test tools (4A, 4B) are taken out from the storage space (11, 12) and a state in which the test tools (4A, 4B) are not taken out from the storage space.

17 Claims, 12 Drawing Sheets

FOREIGN PATENT DOCUMENTS

| | | |
|---|---|---|
| JP | 63-38161 | 2/1988 |
| JP | 1-266697 | 10/1989 |
| JP | 6-65990 | 8/1994 |
| JP | 9-325152 | 12/1997 |
| JP | 2954436 | 7/1999 |
| JP | 2000-35433 | 2/2000 |
| JP | 3036353 | 2/2000 |
| JP | 3331253 | 7/2002 |

\* cited by examiner

ANALYZER-FEEDING DEVICE

TECHNICAL FIELD

The present invention relates to an analyzer-feeding device provided with storage portions to store a plurality of test tools and provided with a transporting member to take out and transport analyzers from the storage portions.

BACKGROUND ART

Urinalysis can be performed by impregnating a reagent pad of a test tool with urine, and then checking the color change of the pad by an optical method. Such optical urinalysis may be performed by using an analytical apparatus in which test tools are successively transported to a measurement point, where the color change of the reagent pad is automatically checked. Such an analytical apparatus often incorporates a test tool feeder for automatically feeding test tools to the measurement point.

FIG. 11 of the present application shows an example of a test tool feeder (See JP-A 2000-35433, for example). The illustrated test tool feeder 9 includes a rotating member 92 formed with a groove 91 for receiving a single test tool 90, and a storage portion 93 for accommodating a plurality of test tools 90. In the test tool feeder 9, by rotating the rotating member 92, the groove 91 is brought to a position corresponding to the storage portion 93, whereby one of the test tools 90 is received in the groove 91. When the rotating member 92 is rotated further from this state, the test tool 90 falls from the rotating member 92 to slide down on a slope 94. In this way, in the test tool feeder 9, the test tools 90 are taken out from the storage portion 93 one by one by successively rotating the rotating member 92.

The test tool feeder 9 is designed to store a single kind of test tools 90 in the storage portion 93 and take out the single kind of test tools. Therefore, to use test tools of a kind different from those currently used, it is necessary to remove the test tools from the storage portion 93 and load the different kind of test tools into the storage portion 93. Therefore, in changing the kind of test tools in the test tool feeder 9, the troublesome work of replacing test tools need be performed, and the operation efficiency is deteriorated.

To solve the above problems, a test tool feeder has been proposed which includes a test tool bottle for storing test tools, which is removably mounted so as to be replaced with another bottle when another kind of test tools are to be used (See JP-A-H09-325152, for example). Although this kind of test tool feeder can eliminate the troublesome work of changing the test tools, it suffers another troublesome work of changing test tool bottles, and hence, still has room for improvement.

DISCLOSURE OF THE INVENTION

An object of the present invention is to provide a test tool feeder which makes it possible to use different kinds of test tools without requiring the user's troublesome work.

According to a first aspect of the present invention, there is provided a test tool feeder comprising: a storage portion for storing a plurality of test tools; and a transporting member provided with at least one loading portion for loading the test tools stored in the storage portion, where the transporting member transports the test tools one by one. The storage portion includes a plurality of storage spaces each storing a plurality of test tools.

Preferably, in the test tool feeder, each of the storage spaces is selectively brought into a state in which the test tools are taken out from the storage space and a state in which the test tools are not taken out from the storage space.

According to a second aspect of the present invention, there is provided a test tool feeder comprising a storage portion for storing a plurality of test tools, and a transporting member for transporting the test tools individually. In the test tool feeder, selection can be made between a state in which the test tools are taken out from the storage space and a state in which the test tools are not taken out from the storage space.

For instance, the state in which the test tools are not taken out from the storage space is achieved by lifting the test tools stored in the storage space so that the test tools do not come into contact with the transporting member. The state in which the test tools are taken out from the storage space is achieved by bringing at least some of the test tools stored in the storage space into contact with the transporting member.

For instance, the transporting member comprises a rotating member. The transporting member may transport the test tools horizontally.

The test tool feeder according to the present invention may further comprise a movable member for lifting the test tools stored in at least one of the plurality of storage spaces.

The movable member may include at least one pivotable lift portion. In this case, the transporting member includes a recess for receiving the lift portion.

For instance, in the test tool feeder according to the present invention, the test tools stored in the storage space are held in contact with the transporting member when the lift portion is received in the recess, whereas the test tools stored in the storage space are lifted by the movable member so as not to come into contact with the transporting member when the lift portion is not received in the recess.

The lift portion of the movable member is held in contact with the transporting member by gravity. The lift portion of the movable member may be pivoted by an actuator.

In the case where the transporting member comprises a rotating member, the lift portion is positioned closer to the center of the rotating member than the circumferential surface of the rotating member when the lift portion is received in the recess. In the case where the transporting member transports the test tools horizontally, the lift portion is positioned lower than an upper surface of the transporting member when the lift portion is received in the recess.

For instance, the selection between the state in which the test tools are taken out from the storage space and the state in which the test tools are not taken out from the storage space is made by controlling the movable range of the at least one loading portion.

For instance, the plurality of storage spaces include a first and a second storage spaces. For instance, the at least one loading portion includes a first loading portion for loading the test tools stored in the first storage space, and a second loading portion for loading the test tools stored in the second storage space.

The first storage space and the second storage space are separated by a partition member disposed in the storage portion. In this case, the movable member is supported by the partition member. For instance, the movable member may be capable of lifting the test tools stored in one of the first and the second storage spaces.

In the case where the transporting member comprises a rotating member, the rotating member may be made rotatable in both a forward direction and a reverse direction. Preferably, in this case, the test tool feeder further comprises a rotation controller for controlling a rotation direction and a rotation angle of the rotating member to control the movable range of the first and the second loading portions.

For instance, the rotation controller controls the rotation direction and the rotation angle of the rotating member in a first movable range in which the lift portion is held in contact with a circumferential surface of the rotating member or in a second movable range in which the lift portion is received in the recess. In the first movable range, test tools are not taken out from the first storage space while test tools are taken out from the second storage space. In the second movable range, test tools are taken out from the first storage space while test tools are not taken out from the second storage space.

The at least one lift portion includes a first lift portion for lifting the plurality of test tools stored in the first storage space, and a second lift portion for lifting the plurality of test tools stored in the second storage space. In this case, the first and the second lift portions may be pivoted by an actuator.

When one of the first and the second lift portions lifts the test tools stored in the first and the second storage spaces, the other one of the first and the second lift portions does not lift the test tools stored in the first and the second storage spaces.

BEST MODE FOR CARRYING OUT THE INVENTION

Best mode for carrying out the present invention will be described below as a first though a fifth embodiments with reference to the accompanying drawings.

First, referring to FIGS. 1-6, a first embodiment of the present invention will be described.

Figure 1:
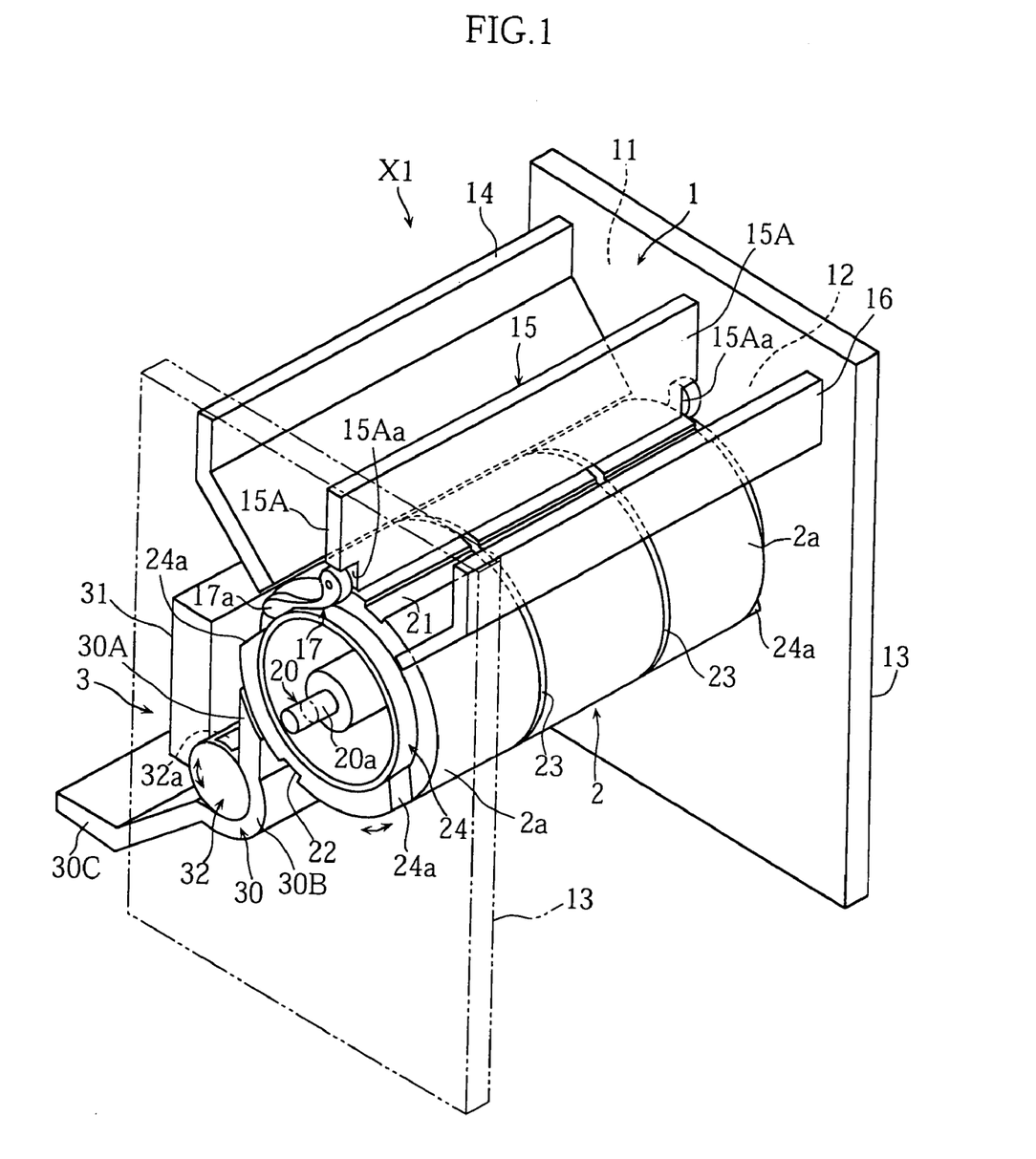
FIG. 1 is an entire perspective view, partially in phantom, of a test tool feeder according to a first embodiment of the present invention.
Figure 2:
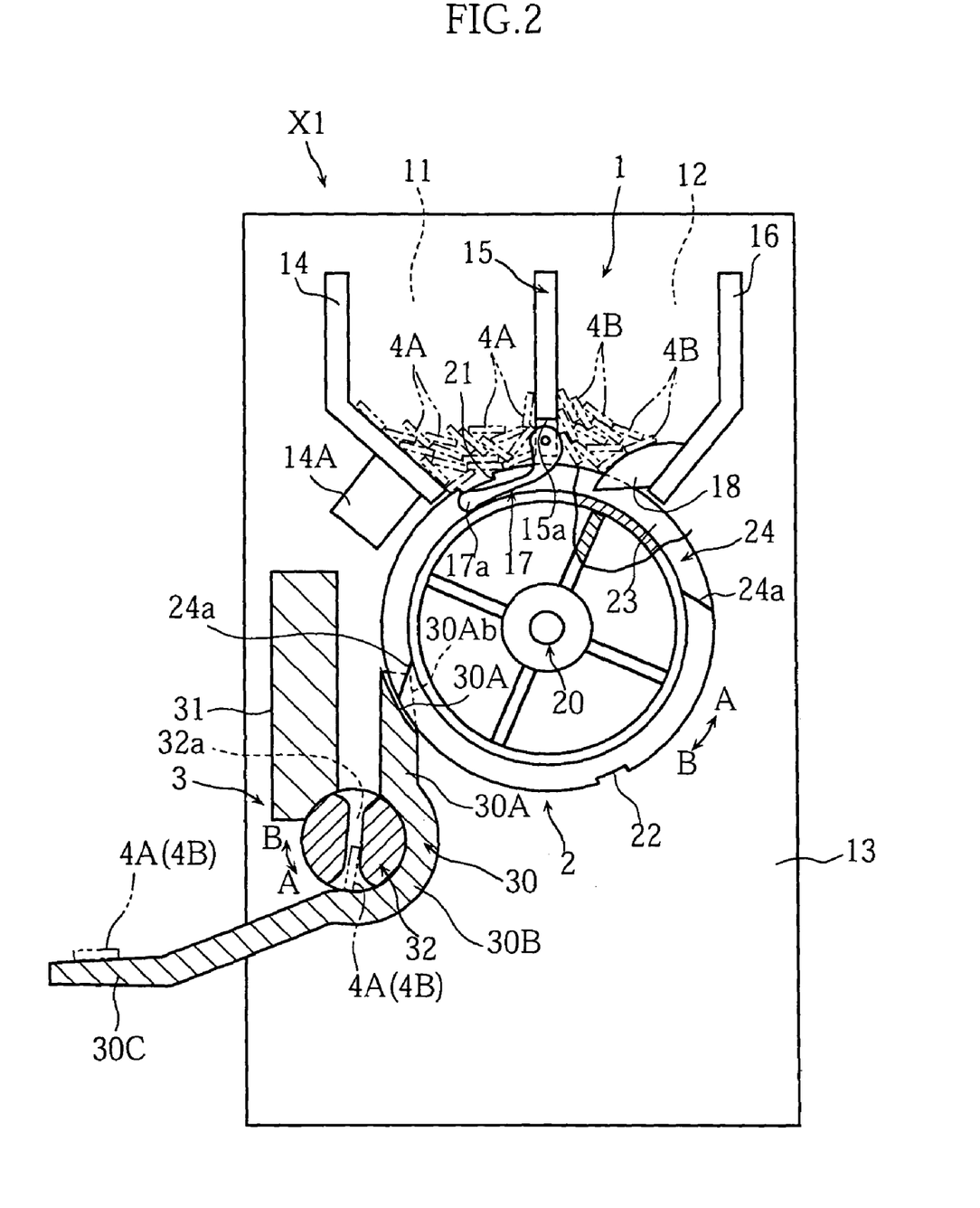
FIG. 2 is a side view, partially in section, of the test tool feeder shown in FIG. 1.
Figure 3:
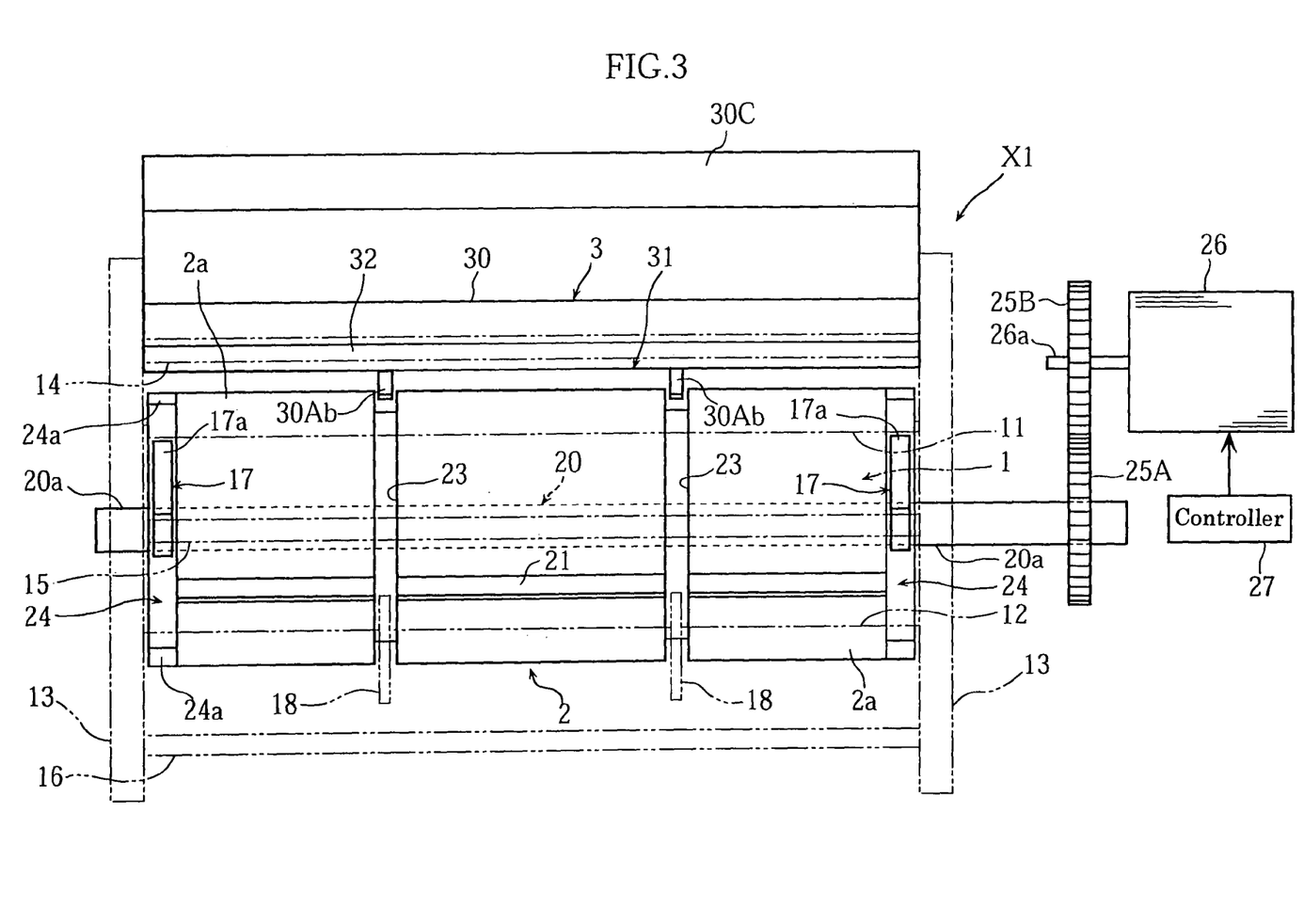
FIG. 3 is a plan view, partially in phantom, of the test tool feeder shown in FIG. 1.

The test tool feeder X1 shown in FIGS. 1-3 is used as incorporated in or connected to an analytical apparatus, for example. Though not illustrated in the figures, each of test tools 4A, 4B to be transported by the test tool feeder X1 comprises a base member in the form of a strip on which one or a plurality of reagent pads are provided.

The test tool feeder X1, designed to choose a desired kind of test tools from two kinds of test tools 4A and 4B, and to transport and feed the test tools 4A or 4B one by one, includes a storage portion 1, a rotating member 2 and a secondary transport mechanism 3.

The storage portion 1 stores a plurality of test tools 4A, 4B (See FIG. 2B) and includes a first and a second storage spaces 11 and 12. The first and the second storage spaces 11 and 12 are provided adjacent to each other above the rotating member 2. The first and the second storage spaces 11 and 12 are defined by two support members 13 and a first through a third members 14-16 fixed between the support members 13. The first and the second storage spaces 11 and 12 store different kinds (for e.g., different inspection items) of test tools 4A and 4B (See FIG. 2).

As shown in FIG. 2, a detector 14A is attached to the first member 14. The detector 14A detects whether or not a test tool 4A, 4B (See FIG. 2) is being transported by the rotating member 2, while also detecting whether the test tool 4A, 4B (See FIG. 2) being transported by the rotating member 2 is showing its obverse side or reverse side. The detector 14A may not necessarily be provided at the first member 14.

As shown in FIGS. 1 and 2, the second member 15 is formed with cutouts 15Aa at its both ends 15A. In each of the cutouts 15Aa, a pivot arm 17 is provided. The arm 17, including a lift portion 17a, is utilized for lifting the test tools 4A (See FIG. 2) stored in the first storage space 11. The lift portion 17a is held in contact with the rotating member 2 by gravity due to its own weight.

As shown in FIGS. 2 and 3, the third member 16 is provided with guide pieces 18 projecting into the second storage space 12. The guide pieces 18 regulate the rotational state of the rotating member 2 by cooperating with grooves 23 of the rotating member 2, as described below, and prevent the test tools 4B stored in the second storage space 12 (See FIG. 2) from being unintentionally taken out from the second storage space 12 when the rotating member 2 is rotated in a backward direction B.

As shown in FIGS. 1-3, the rotating member 2 is utilized for taking out and transporting the test tools 4A, 4B one by one from the storage portion 1. The rotating member 2 includes a rotation shaft 20, a first and a second loading portions 21, 22, a plurality of grooves 23 (two grooves in the figures) and cutouts 24.

The rotation shaft 20 supports the rotating member 2 between the support members 13 and has its ends 20a rotatably inserted in the support members 13. As shown in FIG. 3, the rotation shaft 20 is connected to a motor 26 via gears 25A and 25B. The motor 26 is controlled by a controller 27 to regulate the rotation direction and rotation output of the rotation shaft 26a. Thus, the rotating member 2 is rotatable in the forward direction A and the backward direction B by the rotational force from the motor 26.

The rotation of the rotating member 2 in the forward direction A and the backward direction B may be controlled by changing the meshing of gears in a gear mechanism provided between the rotation shaft 20 of the rotating member 2 and the motor 26.

As shown in FIGS. 1 and 3, each of the first and the second loading portions 21 and 22, formed in the cylindrical surface of the rotating member 2 to extend axially of the rotating member 2, is used for carrying one test tool 4A, 4B stored in the first or the second storage space 11 or 12. As shown in FIGS. 1 and 2, the first and the second loading portions 21 and 22 are provided at positions symmetrical with respect to the rotation shaft 20, as viewed in the axial direction of the rotating member 2. Specifically, the first loading portion 21 is formed at a middle of a first region of the cylindrical surface of the rotating member 2, the region formed with the cutouts 24, whereas the second loading portion 22 is formed at a middle of a second region of the cylindrical surface of the rotating member 2, the region without the cutouts 24. The first and the second loading portions 21 and 22 change their positions in accordance with the rotation of the rotating member 2. The positions and movable ranges of the first and the second loading portions 21 and 22 can be controlled by controlling the rotation direction and rotation angle of the rotating member 2.

As shown in FIGS. 2 and 3, the guide grooves 23 receive the guide pieces 18 of the third member 16 and blades 30Ab of the secondary transport mechanism 3, as described later, and the grooves are formed in the cylindrical surface of the rotating member 2 to entirely circle the cylindrical member circumferentially. Thus, in rotating the member 2, the guide pieces 18 and the blades 30Ab do not interfere with the rotation of the rotating member 2, while also preventing the rotating member 2 from moving in the axial direction of the rotating member 2.

Figure 4A:
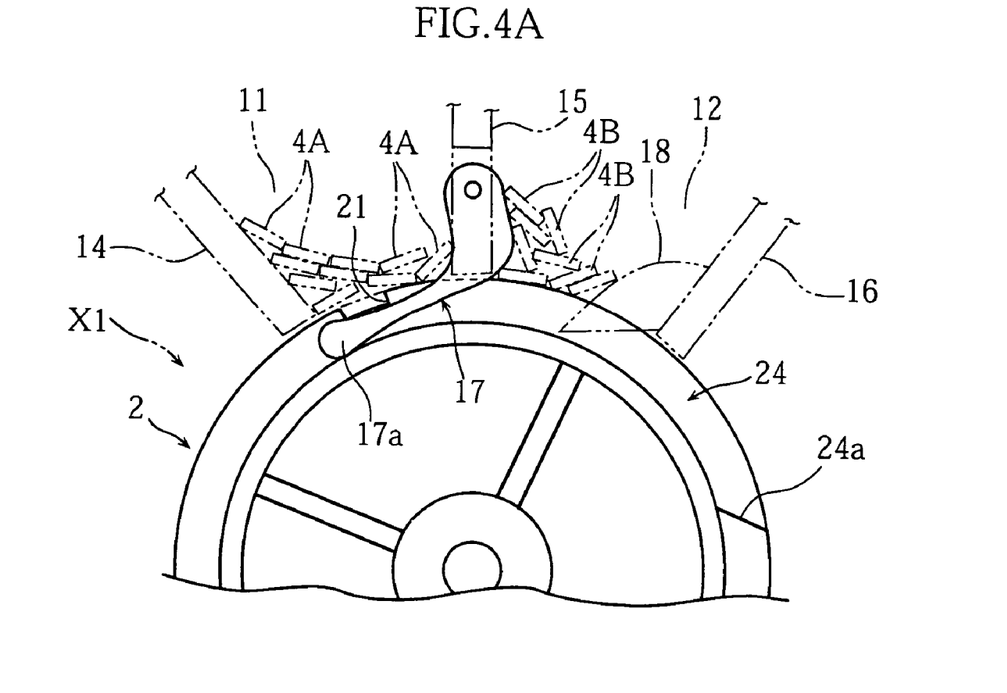
FIGS. 4A and 4B are side views of a principal portion for describing the operation of an arm and a cutout of the rotating member of the test tool feeder shown in FIG. 1.
Figure 4B:
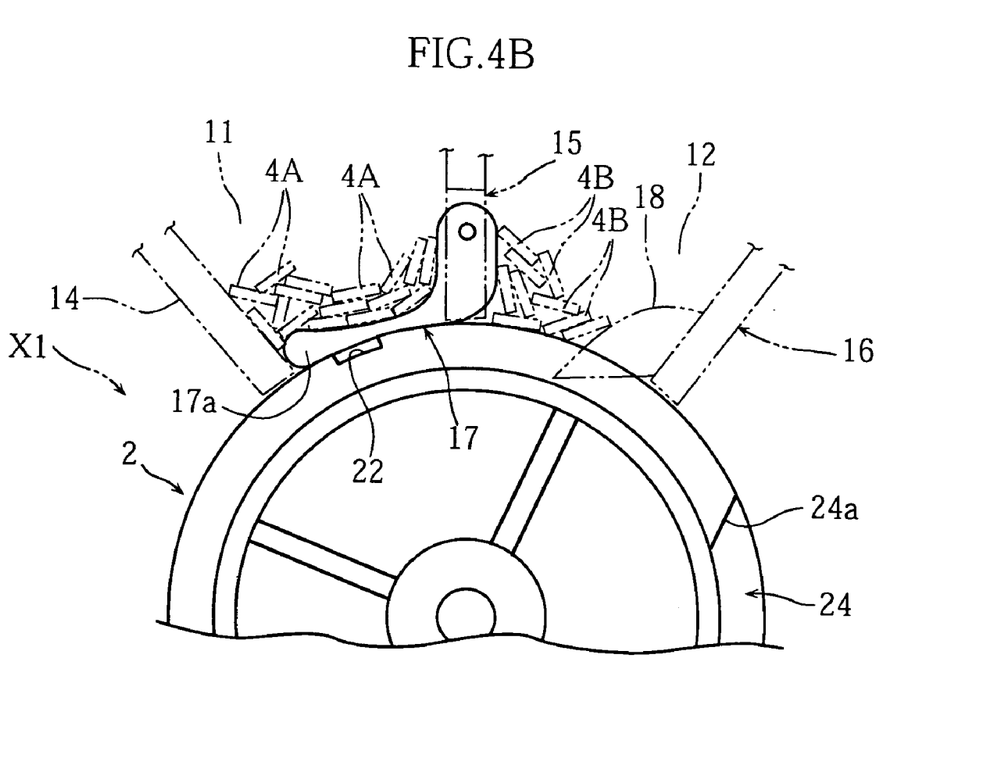

The cutouts 24 can accommodate the lift portions 17a of the arms 17. The cutouts 24 are formed at axially opposite ends 2a of the rotating member 2 and extend along a substantially one half of the circumference. Therefore, by appropriately positioning the cutouts 24 through the rotation of the rotating member 2, it is possible to choose one of two states, i.e., the state in which the lift portions 17a of the arms 17 are received in the cutouts 24 as shown in FIG. 4A and the state in which the lift portions 17a of the arms 17 ride on the circumferential surface of the rotating member 2 as shown in FIG. 4B. The ends 24a of each cutout 24 in the circumferential direction are formed as inclined surfaces. Therefore, when the rotating member 2 is rotated, the transition between the state shown in FIG. 4A and the state shown in FIG. 4B is smooth.

As shown in FIG. 4A, the depth (dimension in the radial direction of the rotating member 2) of the cutouts 24 is so set that the lift portions 17a of the arms 17 is located radially inward relative to the circumferential surface of the rotating member 2. Therefore, when the lift portions 17a of the arms 17 are received in the cutouts 24, it is possible to load the test tools 4A of the first storage space 11 onto the first loading portion 21 without being hindered by the arms 17. When the lift portions 17a of the arms 17 ride on the circumferential surface of the rotating member 2 as shown in FIG. 4B, the test tools 4A in the first storage space 11 are lifted by the arms 17. With such an arrangement, when the rotating member 2 is rotated, the second loading portion 22 moves under the arms 17, so that the test tools 4A are not loaded into the second loading portion 22. Therefore, in the test tool feeder X1, by adjusting the positional relationship between the arms 17 and the cutouts 24, selection can be made between the state in which the test tools 4A are taken out from the first storage space 11 and the state in which the test tools 4A are not taken out.

Figure 5A:
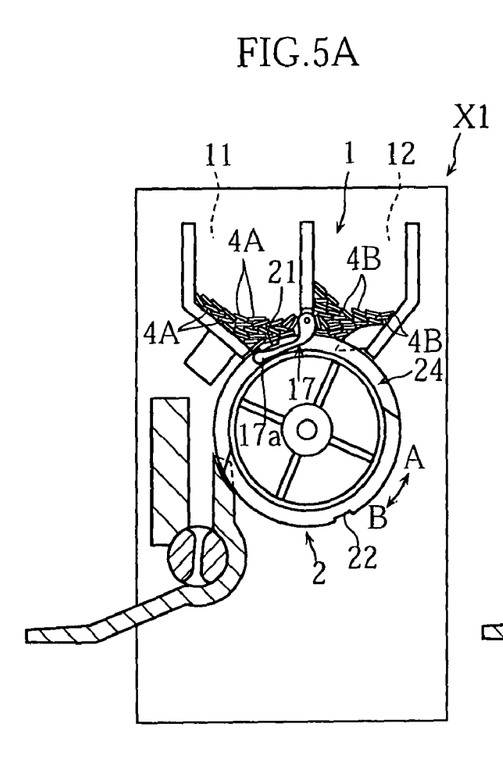
FIGS. 5A-5C are partially sectional views for describing the operation to take out and transport test tools from a first storage space of the test tool feeder shown in FIG. 1.
Figure 5B:
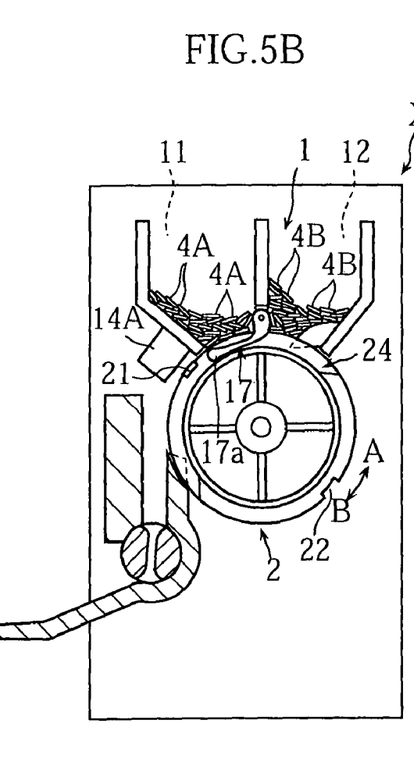
Figure 5C:
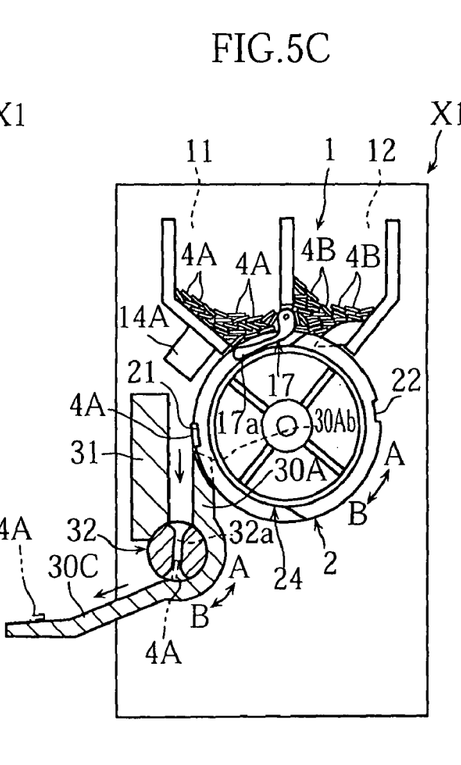

As noted above, in the rotating member 2, cutouts 24 are formed over a substantially one half of the circumference of the rotating member 2, and the first and the second loading portions 21 and 22 are formed at the center of the first region (which is formed with the cutouts 24) or the second region (which is not formed with the cutouts 24) of the circumferential surface of the rotating member 2. Therefore, as understood from FIGS. 5A-5C showing the operation for taking out the test tools 4A from the first storage space 11, when the rotating member 2 is rotated within a range in which the lift portions 17a of the arms 17 are received in the cutouts 24, the second loading portion 22 does not come under the second storage space 12. Therefore, during the rotation within this rotation range, the test tools 4B are not taken out from the second storage space 12. On the other hand, as understood from FIGS. 6A-6D showing the operation for taking out the test tools 4B from the second storage space 12, when the rotating member 2 is rotated within a range in which the lift portions 17a of the arms 17 ride on the circumferential surface of the rotating member 2, the second loading portion 22 can position under the second storage space 12, while the test tools 4A in the first storage space 11 are lifted. Therefore, during the rotation within this rotation range, the test tools 4B can be taken out from the second storage space 12 and transported.

As shown in FIGS. 1 and 2, the secondary transport mechanism 3 defines a path along which the test tools 4A, 4B taken out from the first and the second storage spaces 11, 12 by the rotating member 2 are transported to an intended position. The secondary transport mechanism 3 includes a main body 30, a block member 31 and a reverse member 32.

The main body 30 includes a standing portion 30A, a holder portion 30B and a final transport portion 30C. The standing portion 30A guides the test tools 4A, 4B loaded on the first or the second loading portion 21, 22 to the reverse member 32. As shown in FIGS. 2 and 3, the standing portion 30A has an end 30Aa provided with blades 30Ab. The blades 30Ab serve to scrape off the test tools 4A, 4B from the first or the second loading portions of the rotating member 2. As noted above, the blades 30Ab are arranged to be received in the grooves 23 of the rotating member 2. As shown in FIGS. 1 and 2, the holder portion 30B rotatably holds the reverse member 32. The final transport portion 30C is utilized for transporting the test tools 4A, 4B from the reverse member 32.

The block member 31 prevents the test tools 4A, 4B unloaded from the rotating member 2 from falling out of the secondary transport mechanism 3. The block member 31 is disposed to face the standing portion 30A of the main body 30.

The reverse member 32, having a columnar appearance, turns over the test tool in accordance with the detection result from the detector 14A. The reverse member 32 is formed with a storage space 32a which penetrates the reverse member in the radial direction and extends in the axial direction of the reverse member. Thus, the test tool 4A, 4B dropped from the rotating member 2 is stored in the storage space 32a of the reverse member 32 and turned over, as required, by rotating the reverse member 32 in an appropriate direction. The rotational force from a motor is transmitted to the rotation shaft (not shown) of the reverse member 32. Thus, the reverse member 32 is rotatable in the forward direction A and the backward direction B by the output from the motor. The control of rotation of the reverse member 32 in the forward direction A and the backward direction B may be performed in a similar manner to the control of rotation of the rotating member 2. As the motor, the motor 26 (See FIG. 3) for rotating the rotating member 2 may be utilized. Alternatively, another motor may be provided separately from the motor 26 (See FIG. 3) for rotating the rotating member 2.

As noted above, the test tool feeder X1 chooses a required kind of test tools 4A or 4B from two kinds of test tools 4A and 4B respectively stored in the first and the second storage spaces 11 and 12, and transport and feed the chosen test tools 4A or 4B one by one. The first transport operation for selectively taking out and transporting the test tools 4A from the first storage space 11 will be described below with reference to FIGS. 5A-5C, whereas the second transport operation for selectively taking out and transporting the test tools 4B from the second storage space 12 will be described below with reference to FIGS. 6A-5D.

The choice of the first transport operation or the second transport operation may be performed by the user's operation of an operation button (not shown) provided at the test tool feeder X, for example. Alternatively, the choice of the first transport operation or the second transport operation may be performed automatically by the test tool feeder X. Specifically, the analytical apparatus may read the analyte information applied to the analyte container as a bar code and refers to the host computer for the analyte information. The test tool feeder X may receive the information as to which of the test tools 4A, 4B should be used for the analysis of the analyte and automatically select the test tools 4A or 4B to be used.

As shown in FIGS. 5A-5C, in the first transport operation, the controller 27 (See FIG. 3) restricts the rotation of the rotating member 2 to the range in which the lift portions 17a of the arms 17 are kept received in the cutouts 24 of the rotating member 2. In this state, the test tools 4A are taken out from the first storage space 11 and transported.

Specifically, in the first transport operation, the first loading portion 21 is positioned directly below the first storage space 11, as shown in FIG. 5A, to make the first loading portion ready for receiving the test tool 4A. Preferably, to reliably load the test tool 4A onto the first loading portion 21, the first loading portion 21 is moved reciprocally several times by rotating the rotating member 2 in the forward direction A and the backward direction B through a small angle under the control of the controller 27 (See FIG. 3).

Subsequently, as shown in FIG. 5B, the controller 27 (See FIG. 3) rotates the rotating member 2 in the forward direction A to move the first loading portion 21 to a position which faces the detector 14A. The detector 14A first detects whether or not the test tool 4A is loaded onto the loading portion 21. When the detector 14A detects that the test tool 4A is loaded onto the first loading portion 21, the detector 4A then detects which side i.e., obverse or reverse of the test tool 4A is facing outward. On the other hand, when the detector 14A detects that the test tool 4A is not loaded onto the first loading portion 21, the controller 27 (See FIG. 3) rotates the rotating member 2 in the backward direction B to return the rotating member to the state shown in FIG. 5A, and controls the rotation of the rotating member 2 again to load the test tool 4A onto the first loading portion 21.

After the detector 14A detects which side of the analyzer 4A is facing outward, the controller 27 (See FIG. 3) further rotates the rotating member 2 in the forward direction A to transport the first loading portion 21 and the test tool 4A to a position which faces the block member 31 of the secondary transport mechanism 3, as shown in FIG. 5C. By this rotation, the test tool 4A falls from the first loading portion 21 by gravity due to its own weight or is scraped off by the blades 30Ab of the secondary transport mechanism 3 to be transported into the secondary transport mechanism 3. Specifically, the test tool 4A is guided to the storage space 32a of the reverse member 32 by the block member 31 and the standing portion 30A for storage in the storage space 32a. Then, based on the result of detection by the detector 14A, the reverse member 32 is rotated in the forward direction A or the reverse direction B to transport the test tool 4A to the final transport portion 30C. Specifically, when the detector 14A detects that the obverse side of the test tool 4A is facing outward, the reverse member 32 is rotated in the backward direction B. When the analyzer 4A detects that the reverse side of the test tool 4A is facing outward, the reverse member is rotated in the forward direction A. By such operation, the test tool 4A is transported to the final transport portion 30C with the obverse side thereof facing outward.

As shown in FIGS. 6A-6D, in the second transport operation, the controller 27 (See FIG. 3) restricts the rotation of the rotating member 2 to the range in which the lift portions 17a of the arms 17 ride on the circumferential surface of the rotating member 2. In this state, the test tools 4B are taken out from the second storage space 12 and transported.

Figure 6A:
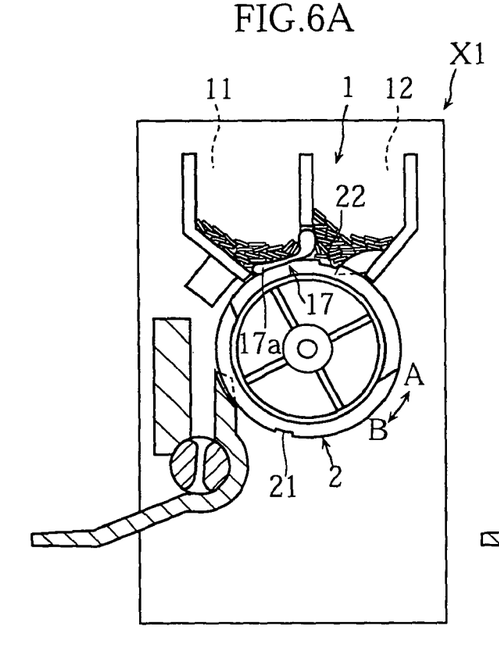
FIGS. 6A-6D are partially sectional views for describing the operation to take out and transport test tools from a second storage space of the test tool feeder shown in FIG. 1.

Firstly, in the second transport operation, the second loading portion 22 is positioned directly below the second storage space 12, as shown in FIG. 6A, to make the second loading portion ready for receiving the test tool 4B. Preferably, to reliably load the test tool 4B onto the second loading portion 22, the second loading portion 22 is moved reciprocally several times by rotating the rotating member 2 in the forward direction A and the backward direction B through a small angle.

Figure 6B:
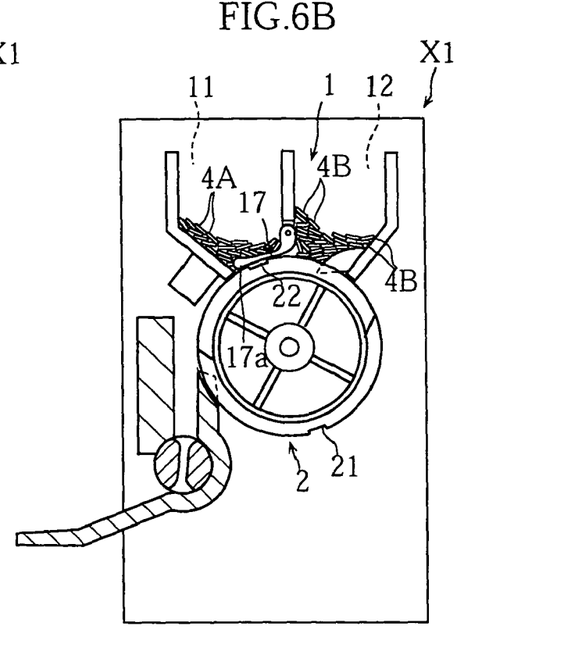

Subsequently, as shown in FIG. 6B, the controller 27 (See FIG. 3) rotates the rotating member 2 in the forward direction A so that the second loading portion 22 passes below the first storage space 11. Since the lift portions 17a of the arms 17 are rest on the circumferential surface of the rotating member 2, the test tools 4A in the first storage space 11 are lifted by the arms 17. Therefore, even when the test tool 4B is not loaded onto the second loading portion 22, the test tool 4A of the first storage space 11 is not loaded onto the second loading portion 22.

Figure 6C:
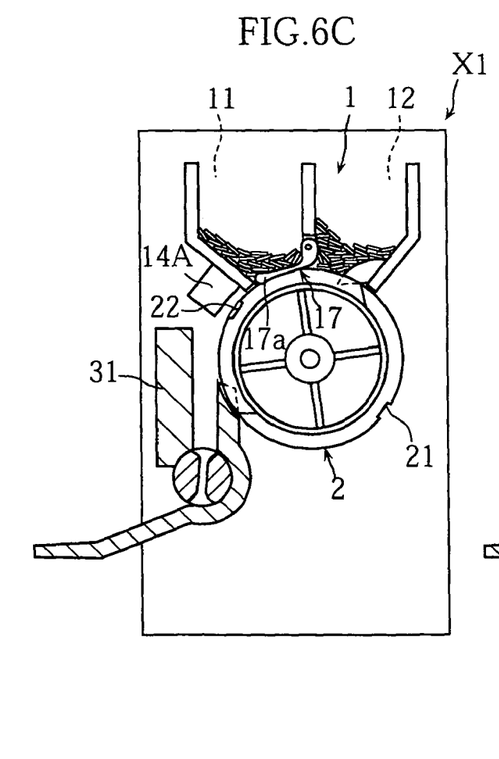
Figure 6D:
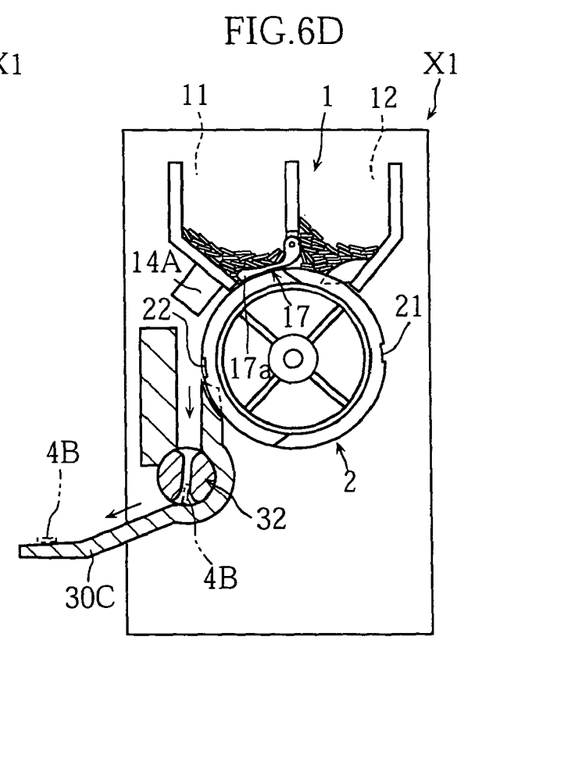

Subsequently, as shown in FIG. 6C, the controller 27 (See FIG. 3) further rotates the rotating member 2 in the forward direction A to move the second loading portion 22 to a position which faces the detector 14A. As can be anticipated from FIGS. 6C and 6D, the subsequent operations are performed similarly to the first transport operation. Specifically, after the detection by the detector 14A, the rotation direction of the reverse member 32 is controlled based on the detection result of the detector 14A to make the obverse side of the test tool 4B face outward, and the test tool 4B is transported to the final transport path 30C.

In the test tool feeder X1, the storage portion 1 can store two kinds of test tools, and the test tools 4A or 4B can be selectively taken out from the relevant storage spaces 11, 12. Therefore, to change the kind of test tools to be fed to e.g. the analytical apparatus, it is only necessary to designate from which of the storage spaces 11 and 12 the test tools 4A, 4B are to be taken out by operating the operation button, for example. Therefore, unlike the prior art device, to change the kind of test tools in the test tool feeder X1, it is unnecessary to replace the test tools stored in the storage portion or replace the test tool bottle attached to the test tool feeder. Therefore, in the test tool feeder X1, the troublesome work to change the kind of test tools can be eliminated, whereby the operation efficiency can be enhanced.

Next, a second embodiment of the present invention will be described with reference to FIGS. 7A and 7B.

Figure 7A:
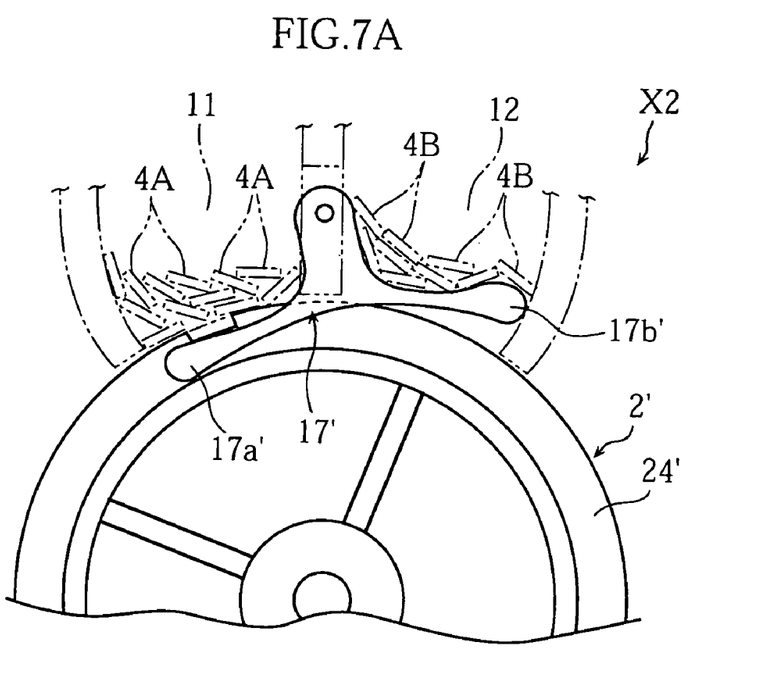
FIGS. 7A and 7B are side views of a principal portion for describing a test tool feeder according to a second embodiment of the present invention.
Figure 7B:
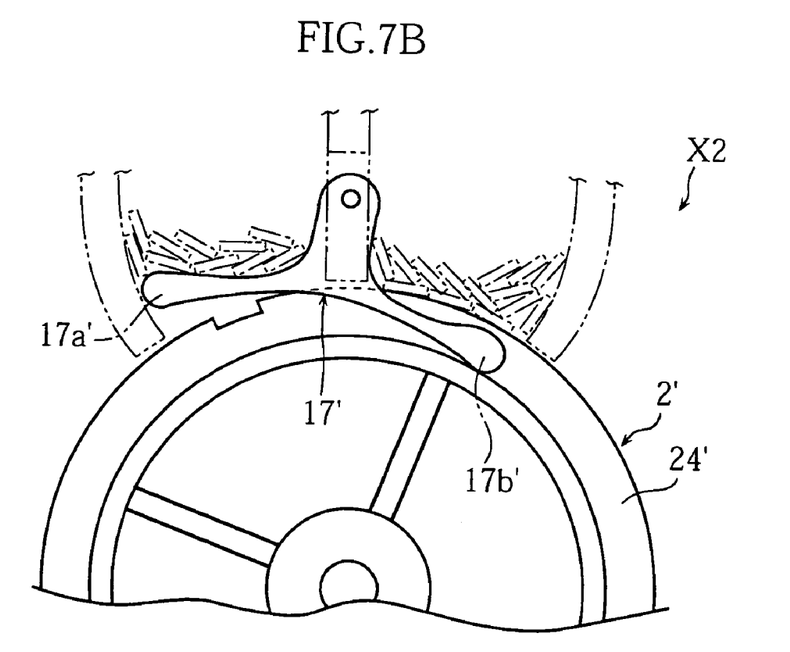

The test tool feeder X2 shown in FIGS. 7A and 7B includes an arm 17' having two lift portions 17a' and 17b', and a rotating member 2' having an end in the axial direction which is formed with a cutout 24' extending over the entire circumference. The arm 17' is driven by a non-illustrated actuator. With such an arrangement, selection can be made between the state in which one of the operative portions 17a' is received in the cutout 24' as shown in FIG. 7A and the state in which the other one of the operative portions 17b' is received in the cutout 24'. Thus, selection can be made between the state in which the test tools 4A of the first storage space 11 are lifted and the state in which the test tools 4B of the second storage space 12 are lifted. Therefore, it is possible to select the state in which the test tools 4A are taken out from the storage space 11 or the state in which the test tools 4B are taken out from the storage space 12.

Next, with reference to FIGS. 8A and 8B and FIGS. 9A and 9B, a third embodiment of the present invention will be described.

Figure 8A:
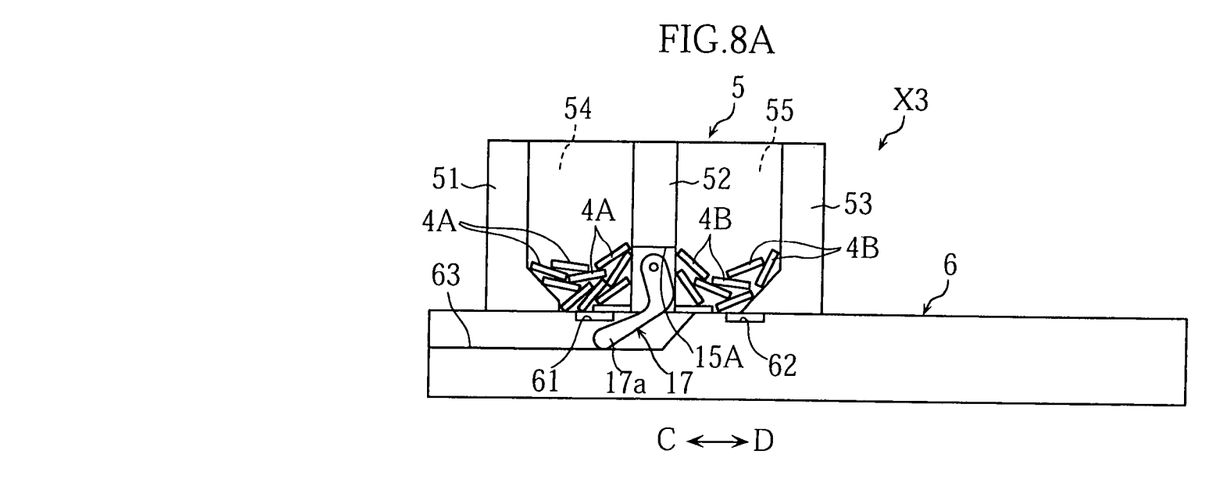
FIGS. 8A and 8B are side views of a principal portion for describing a test tool feeder according to a third embodiment of the present invention.
Figure 8B:
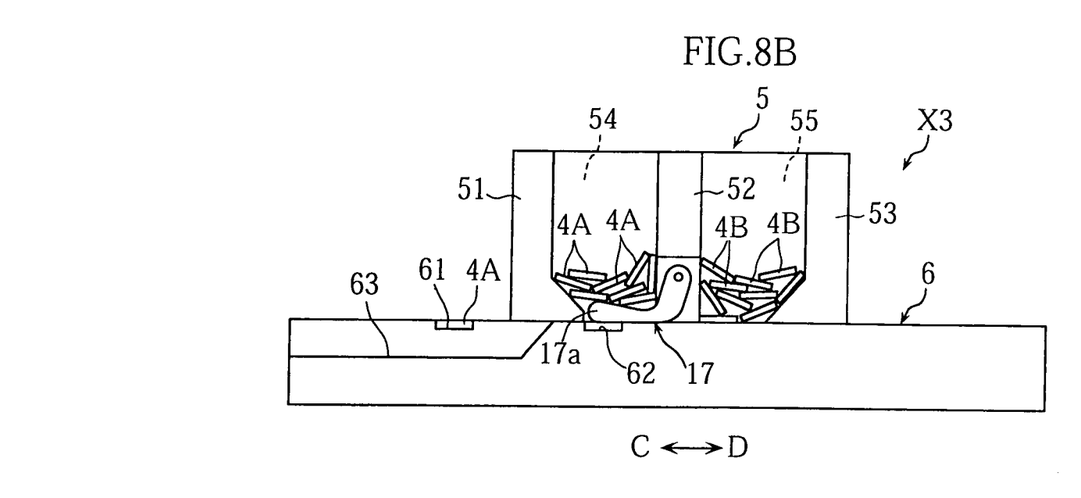

The test tool feeder X3 shown in FIGS. 8A and 8B includes a storage portion 5 and a movable block 6.

The storage portion 5 includes a first through a third walls 51, 52 and 53. The walls 51-53 define a first and a second storage spaces 54 and 55. The first and the second storage spaces 54 and 55 store different kinds of test tools 4A and 4B. The second wall 52 is formed with a cutout 52A. An arm 17 is supported in the cutout 52A.

The block 6 is movable in the arrow CD direction in the figures and includes a first and a second loading portions 61 and 62 and a recess 63. The first loading portion 61 serves to carry the test tools 4A stored in the first storage space 54 and is provided at a position corresponding to the portion formed with the recess 63, as viewed inside. The second loading portion 62 serves to carry the test tools 4B stored in the second storage space 55 and is spaced from the portion formed with the recess 63, as viewed in side. The recess 63 can accommodate the lift portion 17a of the arm 17. By moving the movable block 6 relative to the storage portion 5, selection can be made between the state in which the lift portion 17a of the arm 17 is received in the recess 63 as shown in FIG. 8A and the state in which the lift portion 17a of the arm 17 is not received in the recess 63 but held in contact with the upper surface of the movable block 6 as shown in FIG. 8B.

Figure 9A:
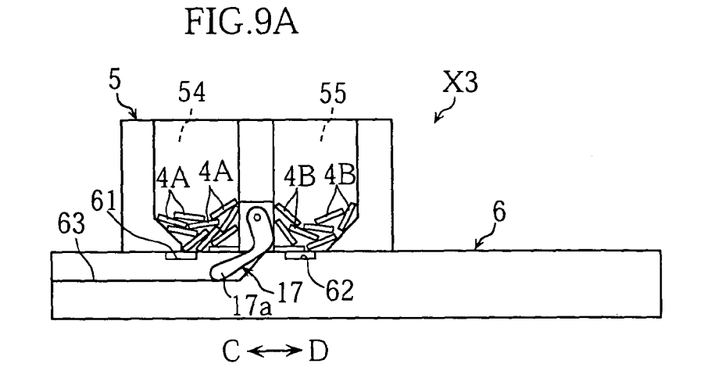
FIGS. 9A-9C are side views of a principal portion for describing a test tool feeder according to the third embodiment of the present invention.
Figure 9B:
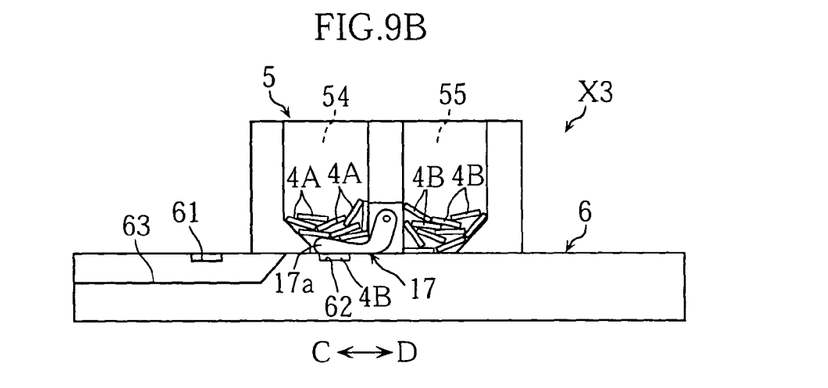

In the test tool feeder X3, by controlling the movement range of the movable block 6, it is possible to select between the state in which the test tools 4A are taken out from the first storage space 54 as shown in FIGS. 8A and 8B and the state in which the test tools 4B are taken out from the second storage space 55 as shown in FIGS. 9A and 9B.

Specifically, to take out the test tools 4A from the first storage space 54, the first loading portion 61 is positioned below the first storage space 54, as shown in FIG. 8A. In this state, the lift portion 17a of the arm 17 is received in the recess 63 so that the test tools 4A are allowed to come into contact with the upper surface of the movable block 6. Therefore, the test tool 4A is loaded onto the first loading portion 61. Subsequently, as shown in FIG. 8B, the movable block 6 is moved in the arrow C direction in the figure, whereby the test tool 4A is taken out from the first storage space 54.

Figure 9C:
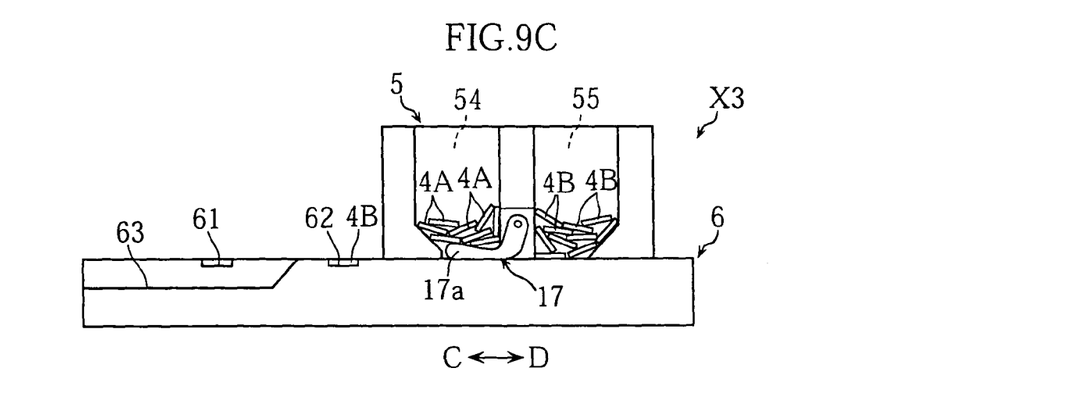

To take out the test tools 4B from the second storage space 55, the second loading portion 62 is positioned below the second storage space 55 as shown in FIG. 9A to load the test tool 4B onto the second loading portion 62. Subsequently, as shown in FIGS. 9B and 9C, the movable block 6 is moved in the arrow C direction in the figures, whereby the test tool 4B is taken out from the second storage space 55. As shown in FIG. 9B, when the movable block 6 moves in the above manner, the second loading portion 62 passes below the first storage space 54. Since the lift portion 17a of the arm 17 is positioned on the upper surface of the movable block 6, the test tools 4A of the first storage space 54 are lifted. Therefore, even when the second loading portion 62 passes below the first storage space 54 without carrying the test tool 4B, the test tool 4A of the first storage space 54 is not loaded onto the second loading position 62.

Next, a fourth embodiment of the present invention will be described below with reference to FIGS. 10A and 10B.

Figure 10A:
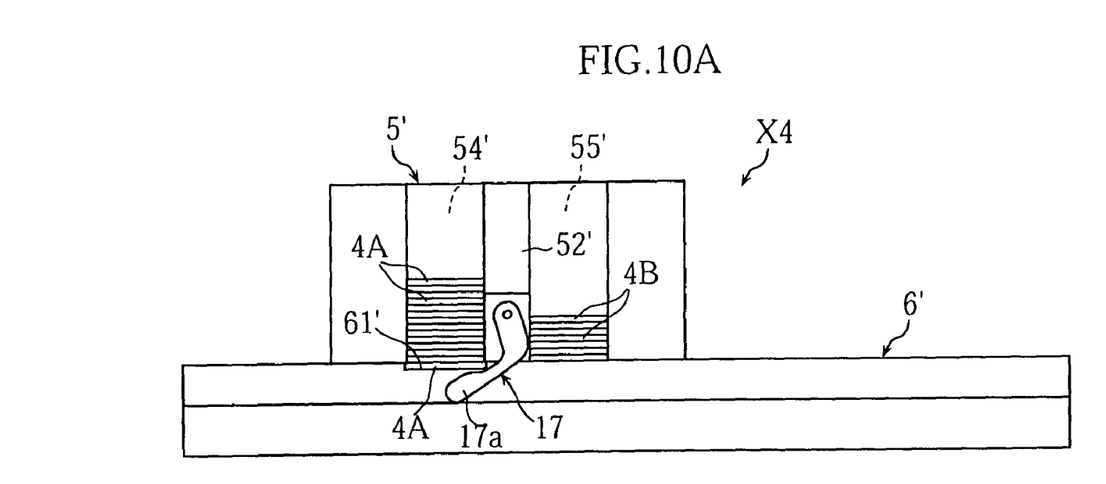
FIGS. 10A and 10B are side views of a principal portion for describing a test tool feeder according to a fourth embodiment of the present invention.
Figure 10B:
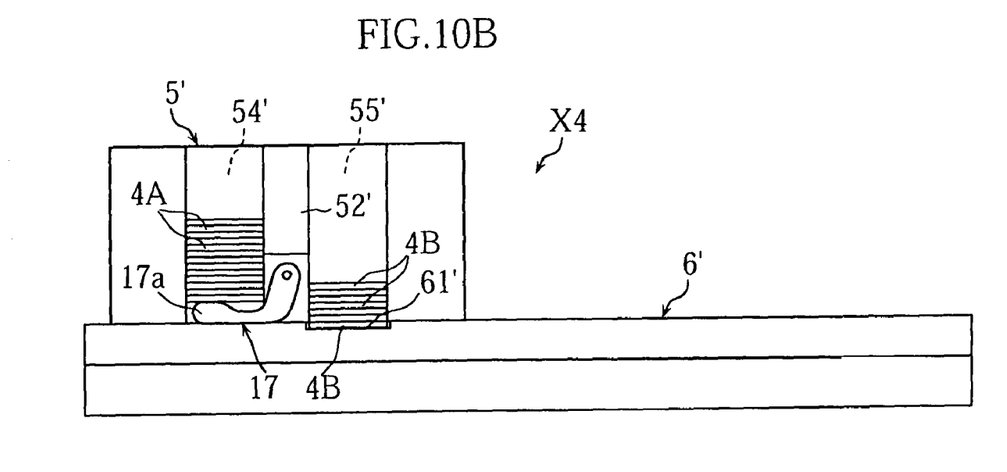

Similarly to the foregoing test tool feeder X3 (See FIG. 8), the test tool feeder X4 shown in FIGS. 10A and 10B includes a storage portion 5' and a movable block 6'.

The storage portion 5' includes a first and a second storage spaces 54' and 55' having a uniform cross section conforming to the configuration, as viewed in plan, of the test tools 4A, 4B. Therefore, the first and the second storage spaces 54' and 55, can store the test tools 4A and 4B in a neatly stacking manner. The storage portion 5' includes a center wall 52' supporting an arm 17. The arm 17 includes a lift portion 17a which can be pivoted by the motive power from a non-illustrated actuator. The movable block 6' includes a single loading portion 61' and a recess 63'.

In the test tool feeder X4, the state in which the test tools 4A are taken out from the first storage space 54' or the state in which the test tools 4B are taken out from the second storage space 55' can be selected by controlling the movement range of the loading portion 61' and selecting the state in which the arm 17 lifts the test tools 4A or the state in which the arm 17 does not lift the test tools 4A.

Next, a fifth embodiment of the present invention will be described below with reference to FIGS. 11A and 11B.

Figure 11A:
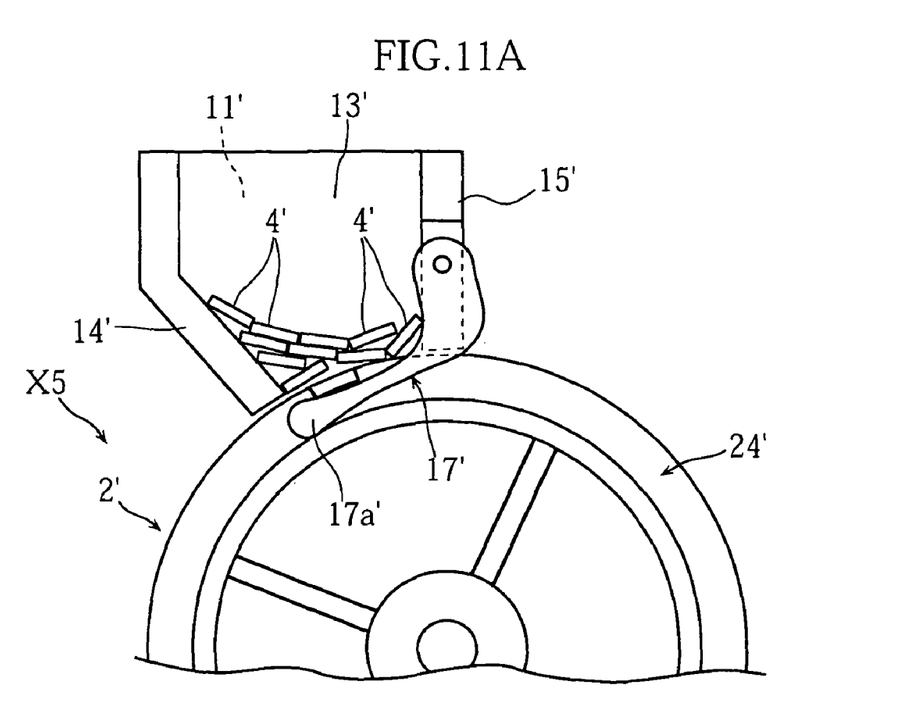
FIGS. 11A and 11B are side views of a principal portion for describing a test tool feeder according to a fifth embodiment of the present invention.
Figure 11B:
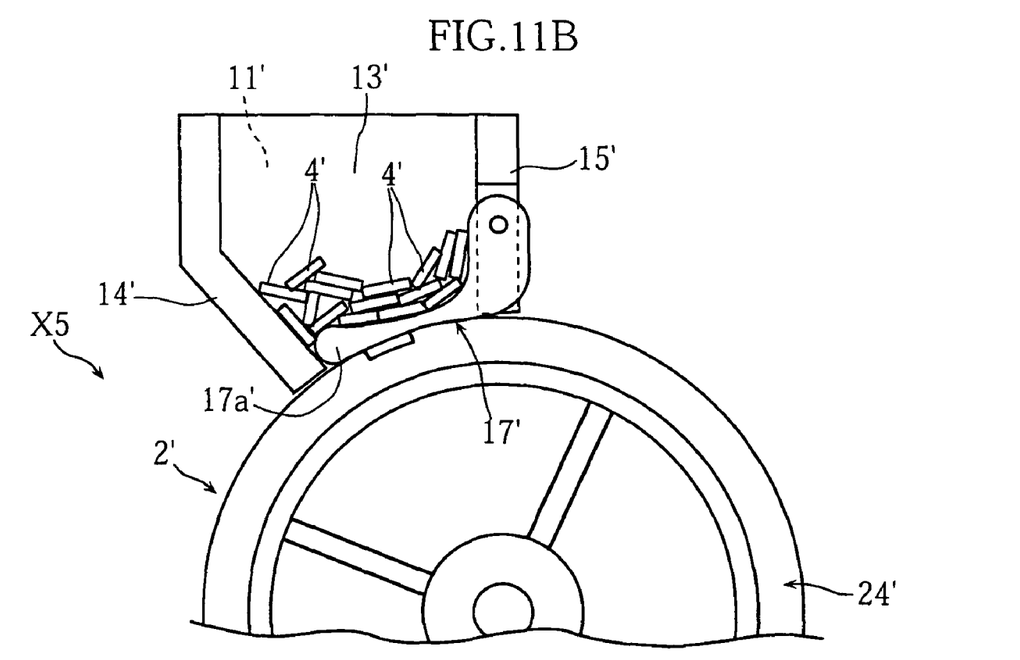
Figure 12:
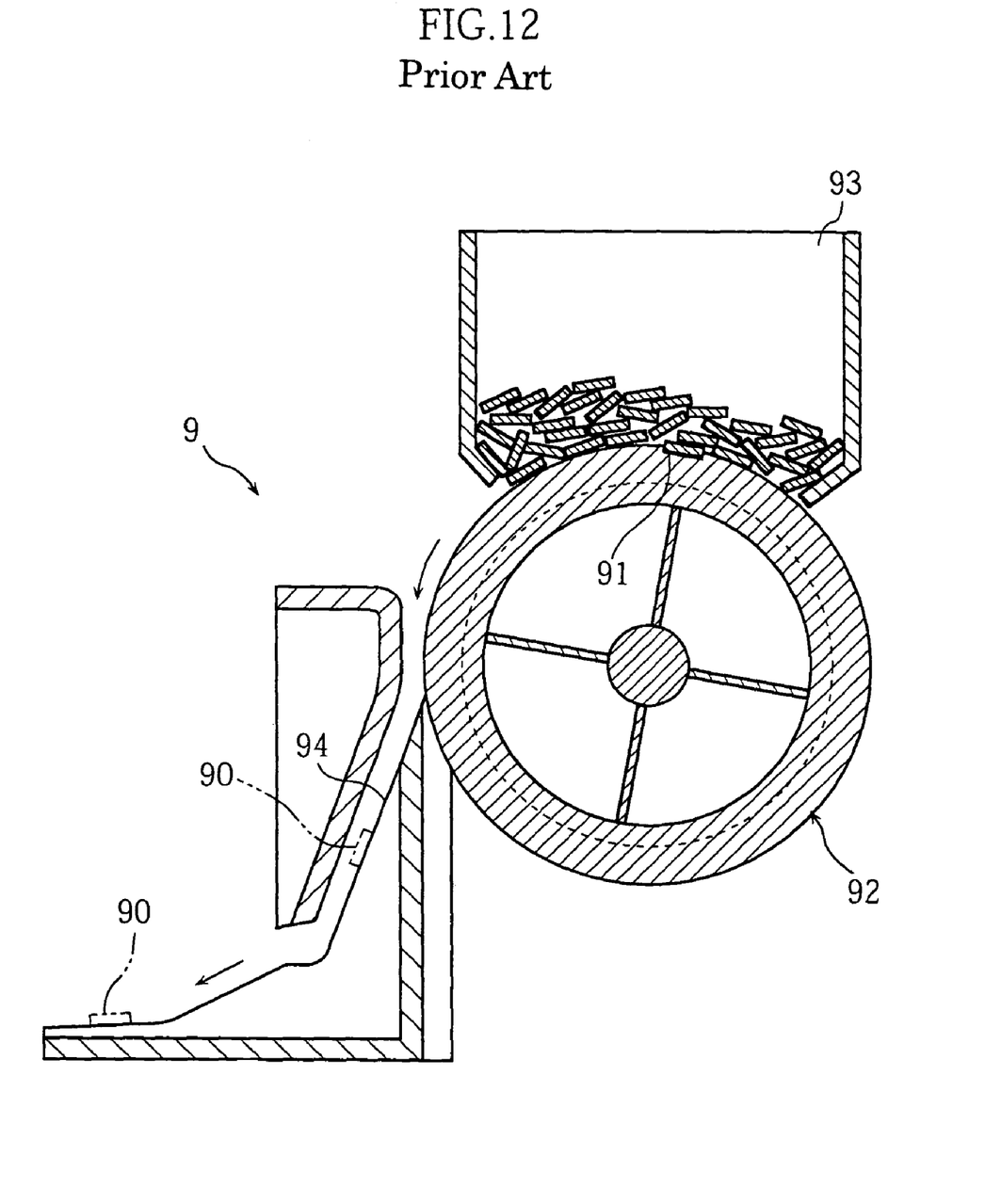
FIG. 12 is a sectional view for describing a conventional test tool feeder.

In the test tool feeder X5 shown in FIGS. 11A and 11B, the storage portion 1' includes a single storage space 11'. The storage space 11' is defined by two support members 13' (only one of the support members 13' is shown in the figures) and a first and a second members 14' and 15' fixed between the support members 13'.

The second support member 15' supports an arm 17'. The arm 17' includes a lift portion 17a' which can be pivoted by a non-illustrated actuator. By the pivotal movement of the lift portion 17a', selection can be made between the state in which the lift portion 17a' is received in a recess 24' of the rotating member 2' and the state in which the lift portion 17' is not received in the recess 24'. The lift portion 17a' lifts the test tools 4' of the accommodation space 11' when not received in the recess 24' and does not lift the test tools 4' when received in the recess 24'.

In the test tool feeder X5, by alternately selecting the state in which the test tools 4' are lifted and the state in which the test tools are not lifted, the test tools 4' in the storage space 11' can be shaken and aligned within the storage space 11'.

The present invention is not limited to the foregoing embodiments and may be modified in various ways. For example, the number of the storage spaces in the storage portion and the number of loading portions may be varied as long as the object can be achieved. For example, three or more storage spaces or loading portions may be provided. When a loading portion passes below the storage space storing unintended test tools, air may be jetted from the rotating member toward the storage space to prevent the unintended test tool from being loaded onto the loading portion.

The member for lifting the test tools is not limited to an arm. For example, a plate member may be disposed to be movable toward and away from the transporting member such as a rotating member or a movable block. In this case, by selecting the position of the plate member, selection can be made between the state in which the test tools are lifted and the state in which the test tools are not lifted. Further, the configuration of the arm is not limited to those described in the foregoing embodiments.

The test tool feeder of the present invention is applicable not only to the feeding of a test piece provided with a reagent pad but also applicable to the feeding of a Lab-on-a Chip or a DNA chip, for example.

The invention claimed is:

1. An analytical testing feeder device comprising:
   a storage portion configured to store a plurality of analytical testing elements;
   a transporting member provided with at least one loading portion configured so that an analytical testing element taken out from the storage portion is loaded in the loading portion, the transporting member configured to transport analytical testing elements one by one;
   a plurality of storage spaces disposed in the storage portion, each storage space configured to store a plurality of analytical testing elements;
   a movable member attached to the storage portion, the movable member includes an at least one lift portion pivotable relative to the storage space;
   wherein each of the storage spaces is selectively brought into a state in which the analytical testing elements are taken out from the storage space and a state in which the analytical testing elements are not taken out from the storage space,
   wherein the movable member is configured so that the state in which the analytical testing elements are not taken out from the storage space is achieved by causing the lift portion to lift the analytical testing elements stored in the storage space so that the analytical testing elements do not come into contact with the transporting member.

2. The analytical testing feeder device according to claim 1, configured so that when the analytical testing elements are taken out from the storage space, at least some of the analytical testing elements stored in the storage space are brought into contact with the transporting member.

3. The analytical testing feeder device according to claim 1, wherein the transporting member comprises a rotating member.

4. The analytical testing feeder device according to claim 3, wherein the rotating member includes a recess that receives the lift portion.

5. The analytical testing feeder device according to claim 4, wherein the lift portion is configured to be out of contact with the analytical testing elements stored in the storage space when the lift portion is received in the recess, and
   wherein the lift portion, when not received in the recess, is configured to lift the analytical testing elements stored in the storage space so that the analytical testing elements are out of contact with the rotating member.

6. The analytical testing feeder device according to claim 5, wherein the movable member is configured to pivot freely relative to the storage portion so that the lift portion of the movable member comes into contact with the rotating member by gravity.

7. The analytical testing feeder device according to claim 6, wherein the plurality of storage spaces include a first storage space and a second storage space, and
   wherein said at least one loading portion includes a first loading portion that loads the analytical testing elements stored in the first storage space, and a second loading portion that loads the analytical testing elements stored in the second storage space.

8. The analytical testing feeder device according to claim 7, wherein the first storage space and the second storage space are separated by a partition member disposed in the storage portion, and
   wherein the movable member is supported by the partition member.

9. The analytical testing feeder device according to claim 7, wherein the rotating member is rotatable in both a forward direction and a reverse direction, and
   wherein the analytical testing feeder device further comprises a rotation controller that controls a rotation direction and a rotation angle of the rotating member to control the movable range of the first and the second loading portions.

10. The analytical testing feeder device according to claim 9, wherein the rotation controller is configured to control the rotation direction and the rotation angle of the rotating member in a first movable range in which the lift portion is held in contact with a circumferential surface of the rotating member or in a second movable range in which the lift portion is received in the recess,
    wherein, in the first movable range, analytical testing elements are not taken out from the first storage space while analytical testing elements are taken out from the second storage space,
    wherein, in the second movable range, analytical testing elements are taken out from the first storage space while analytical testing elements are not taken out from the second storage space.

11. The analytical testing feeder device according to claim 5, wherein the recess is configured to receive the lift portion in a manner such that the lift portion is positioned closer to a center of the rotating member than a circumferential surface of the rotating member.

12. The analytical testing feeder device according to claim 4, wherein the plurality of storage spaces include a first storage space and a second storage space, and
    wherein said at least one lift portion includes a first lift portion that lifts the plurality of analytical testing elements stored in the first storage space and a second lift portion that lifts the plurality of analytical testing elements stored in the second storage space.

13. The analytical testing feeder device according to claim 12, further comprising an actuator that causes the first and the second lift portions to pivot.

14. The analytical testing feeder device according to claim 1, wherein the transporting member comprises a movable block that transports the analytical testing elements horizontally.

15. The analytical testing feeder device according to claim 14, wherein the transporting member includes a recess that receives the lift portion.

16. The analytical testing feeder device according to claim 15, the lift portion is received in the recess so that the lift portion is out of contact with the analytical testing elements stored in the storage space, and
    the lift portion, when is not received in the recess so that the lift portion lifts the analytical testing elements stored in the storage space so that the analytical testing elements are out of contact with the transporting member.

17. The analytical testing feeder device according to claim 16, wherein the recess is configured to receive the lift portion in a manner such that the lift portion is positioned lower than an upper surface of the transporting member.

* * * * *